United States Patent [19]

Kanai

[11] Patent Number: 5,327,792
[45] Date of Patent: Jul. 12, 1994

[54] METHOD OF DISPLAYING MULTI-DIMENSIONAL DISTRIBUTION OF PARTICLES

[75] Inventor: Kazuyuki Kanai, Kasai, Japan

[73] Assignee: Toa Medical Electronics Co., Ltd., Kobe, Japan

[21] Appl. No.: 88,569

[22] Filed: Jul. 1, 1993

[30] Foreign Application Priority Data

Jul. 27, 1992 [JP] Japan .................................. 4-220667

[51] Int. Cl.⁵ ...................... G01N 15/00; G01N 15/02
[52] U.S. Cl. .................................. 73/865.5; 356/335; 356/336
[58] Field of Search ............... 73/865.5; 356/335, 336, 356/337

[56] References Cited

U.S. PATENT DOCUMENTS 4,991,092  2/1991  Greensite ........................ 364/413.22
5,235,508  8/1993  Lirov et al. ..................... 364/474.13

FOREIGN PATENT DOCUMENTS 63-222239  9/1988  Japan .

Primary Examiner—Hezron E. Williams
Assistant Examiner—Daniel S. Larkin
Attorney, Agent, or Firm—Wegner, Cantor, Mueller & Player

[57] ABSTRACT

In the case of forming a distribution diagram based upon measured data consisting of measured values of two or more characteristics of particles and counted values thereof which are obtained by analyzing a specimen intermixedly including plural kinds of particles with a particle analyzing device, by plotting the particles in a co-ordinate system of two or more dimensions having said characteristics as its parameters, a method of collecting the measured data over a specific length of measuring time and seeking a time-related change of the distribution diagram to visually display the same, in which a space defined by the co-ordinate system is partitioned into plural domains, in the measuring time is divided into plural time intervals and the number of the particles belonging to each domain is counted for each time interval, thereby displaying the particle distribution diagram partitioned into domains on a display screen and also displaying a time-related change of the number of particles with a folded-line diagram superposedly in each domain.

3 Claims, 4 Drawing Sheets

| X(1) | | | |
|---|---|---|---|
| N13(1) | N14(1) | N15(1) | N16(1) |
| N9(1) | N10(1) | N11(1) | N12(1) |
| N5(1) | N6(1) | N7(1) | N8(1) |
| N1(1) | N2(1) | N3(1) | N4(1) |

| X(2) | | | |
|---|---|---|---|
| N13(2) | N14(2) | N15(2) | N16(2) |
| N9(2) | N10(2) | N11(2) | N12(2) |
| N5(2) | N6(2) | N7(2) | N8(2) |
| N1(2) | N2(2) | N3(2) | N4(2) |

| X(3) | | | |
|---|---|---|---|
| N13(3) | N14(3) | N15(3) | N16(3) |
| N9(3) | N10(3) | N11(3) | N12(3) |
| N5(3) | N6(3) | N7(3) | N8(3) |
| N1(3) | N2(3) | N3(3) | N4(3) |

| X(4) | | | |
|---|---|---|---|
| N13(4) | N14(4) | N15(4) | N16(4) |
| N9(4) | N10(4) | N11(4) | N12(4) |
| N5(4) | N6(4) | N7(4) | N8(4) |
| N1(4) | N2(4) | N3(4) | N4(4) |

| X(5) | | | |
|---|---|---|---|
| N13(5) | N14(5) | N15(5) | N16(5) |
| N9(5) | N10(5) | N11(5) | N12(5) |
| N5(5) | N6(5) | N7(5) | N8(5) |
| N1(5) | N2(5) | N3(5) | N4(5) |

| X(6) | | | |
|---|---|---|---|
| N13(6) | N14(6) | N15(6) | N16(6) |
| N9(6) | N10(6) | N11(6) | N12(6) |
| N5(6) | N6(6) | N7(6) | N8(6) |
| N1(6) | N2(6) | N3(6) | N4(6) |

METHOD OF DISPLAYING MULTI-DIMENSIONAL DISTRIBUTION OF PARTICLES

BACKGROUND OF THE INVENTION

This invention relates to a method of visually displaying a multi-dimensional spatial distribution of particles obtained by a measuring device such as a particle analyzing device on a plane and, especially, to such method of displaying a time-related change of a three-dimensional spatial distribution.

For example, when a specimen prepared by extracting only leukocytes from blood is passed through a flow cytometer to measure forward and sideward scattered light intensities of each blood-corpuscle and the measured values are plotted on a two-dimensional rectangular co-ordinate plane having the forward and sideward scattered light intensities as its abscissa $X_1$ and ordinate $X_2$, respectively, such a distribution diagram as shown in FIG. 1 is obtained. Since a number of dots in this diagram correspond respectively to the measured corpuscles, the frequency distribution thereof is presumable from the density of the dots. However, if a third axis is established for the frequency, a three-dimensional distribution is obtained and it can be displayed on a plane as a set of sectional views along some planes normal to any axis or a solid diagram such as a topograph. An example of this method is disclosed in Japanese opened patent gazette No. S63(88)-222239 as a method of displaying a time-related change of a frequency distribution of particle volume.

However, a multi-dimensional distribution higher than three-dimension is theoretically possible also since there are more measurable characteristics of the particles. Although such multi-dimensional distributions, especially, those including time as a parameter, are important, it has been a very difficult practice to display them on a two-dimensional display screen or recording paper and no method has been proposed heretofore for this purpose.

Accordingly, an object of this invention is to provide a method of visually displaying a time-related change of a spatial distribution of three or more dimensions in simple and plain fashion through simplified data processing.

SUMMARY OF THE INVENTION

According to a feature of the method of this invention which can achieve the above-mentioned object, at least two characteristics of a number of particles are successively measured first for each particle over a predetermined time interval to obtain a time-sequence of measured data of these characteristics. Then, the predetermined time period is divided into a plurality of small time intervals and, also, a co-ordinate space having the at least two characteristics as its parameters is partitioned into a plurality of small domains. The measured data are plotted in this co-ordinate space to form a spatial distribution of the particles with regard to these parameters and the particles belonging to each domain are counted for each time interval. Thereafter, the spatial distribution is displayed together with boundaries of the small domains and, at the same time, the number of particles in each time interval is displayed in each domain.

These and other features and operation of this invention will be described in more detail below in connection with an embodiment thereof with reference to the accompanying drawings.

DETAILED DESCRIPTION OF PREFERRED EMBODIMENT

Figure 2:
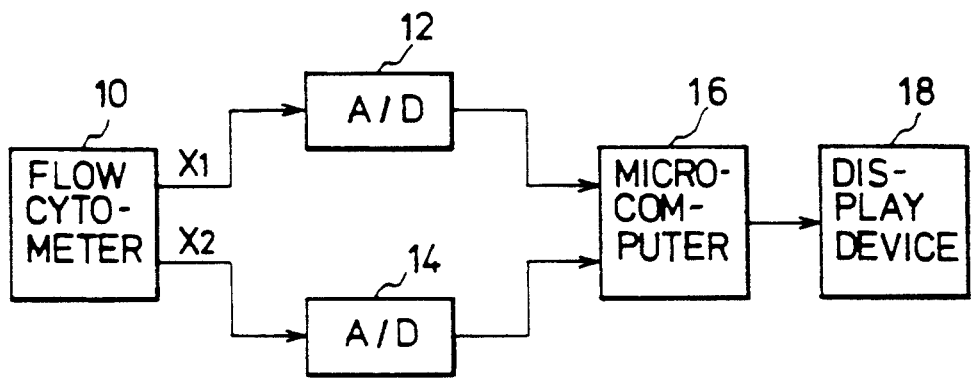
FIG. 2 is a block diagram showing an embodiment of the particle analyzing device used for realizing the method of this invention.

FIG. 2 shows a particle analyzing device for realizing the method of this invention, which includes allow cytometer 10. The flow cytometer 10 is arranged to measure two characteristics, for example, forward and sideward scattered light intensities, of each particle passing therethrough within a predetermined length of time T and output them as a time-sequence of measured signals $X_1$ and $X_2$. The signals $X_1$ and $X_2$ are converted into digital signals by analog-to-digital (A/D) convertors 12 and 14 and supplied to a microcomputer 16. These measured signals will be generalized hereinunder as "measured data X". The microcomputer 16 provides the measured data X with the following processing and displays the result with a display device 18. The display device 18 may be provided with a printing device (not shown) for enabling the display pattern to be printed on a paper.

Figure 3:
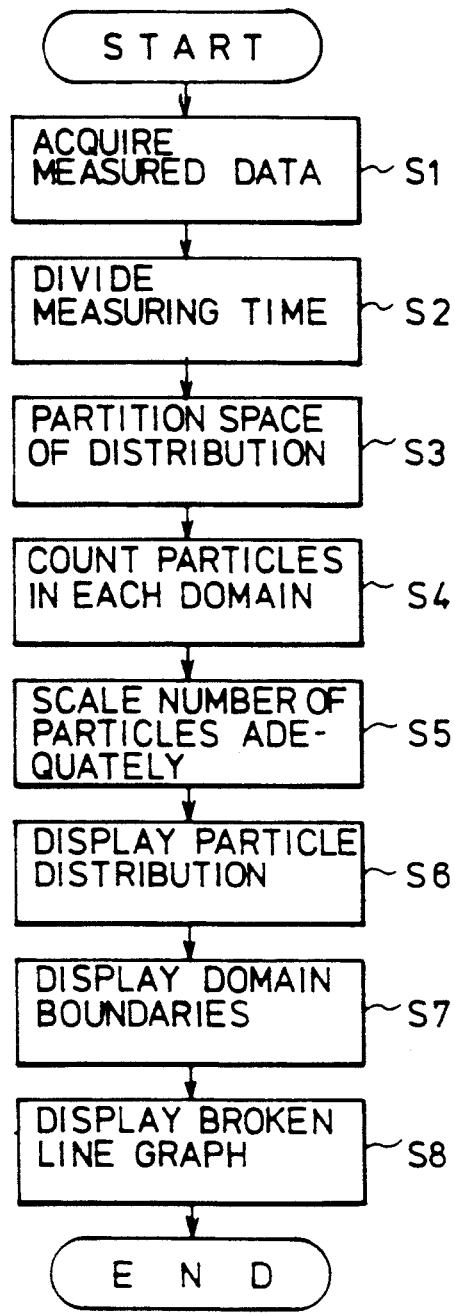
FIG. 3 is a flow chart showing a process for realizing the method of this invention.
Figures 4, 6A, 6B, 6C, 6D, 6E, 6F:
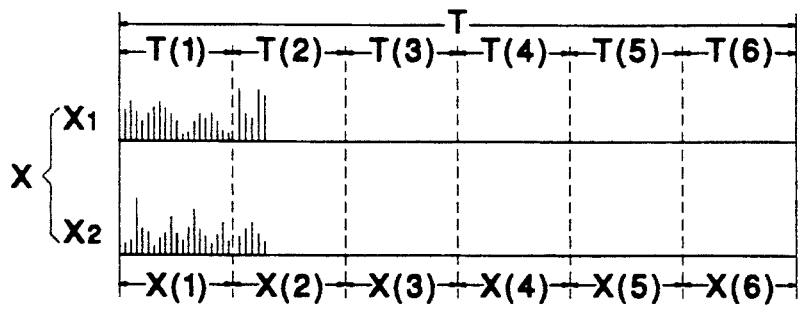
FIG. 4 is a diagram showing a time-sequence of measured data of two characteristics which is divided along the time direction in accordance with the method of this invention.
FIGS. 6A-6F are diagrams illustrative of the number of particles calculated for each divided time interval for each partitioned domain in the two-dimensional distribution of the two characteristics in accordance with the method of this invention.

The processing executed by the microcomputer 16 will be described below with reference to the flow chart of FIG. 3. First of all, the measured data X, namely, the time-sequence of measured signals $X_1$ and $X_2$ are acquired (step S1). FIG. shows the values of these signals $X_1$ and $X_2$ as a form of histogram along a time axis (abscissa). Then, the measuring time T is equally divided by six and the measured data X in the respective time intervals T(i) are referred to as X(i), where i=1, 2, . . . 6, as shown in FIG. 4 (step S2). The number of divided time intervals (six, in this embodiment) may be adequately selected in accordance with the total number of measured particles and complexity of the time-related change of the measured data X.

Figure 1:
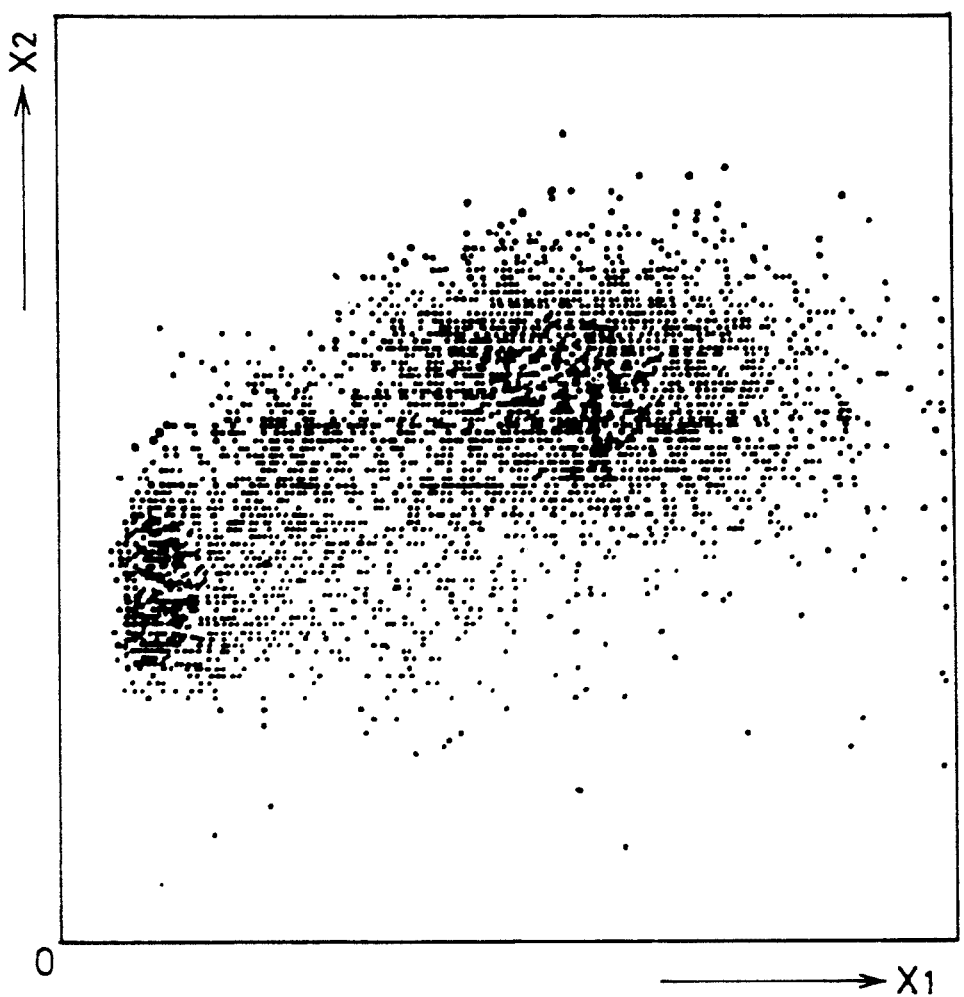
FIG. 1 is a diagram showing an example of two-dimensional distribution obtained from measured data of two characteristics of leukocytes supplied by a flow cytometer.
Figure 5:
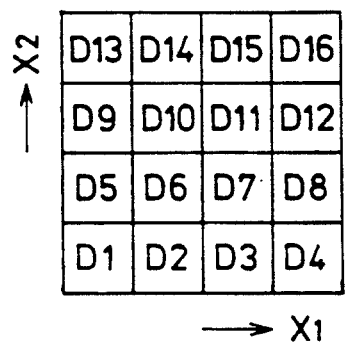
FIG. 5 is a diagram illustrative of a two-dimensional distribution of two characteristics which is partitioned into small domains in accordance with the method of this invention.

In the next step, a two-dimensional rectangular coordinate system having the parameters $X_1$ and $X_2$ as its abscissa and ordinate is established and the measured data X are plotted therein to form a distribution diagram as shown in FIG. 1. All area of the distribution diagram, namely, the square area in FIG. 1 is equally partitioned into sixteen domains in a 4×4 checker board pattern for example, as shown in FIG. 5 and the respective domains are referred to as Dj, where j=1, 2, ... 16 (step S3). Then, the particles contained in each domain Dj are counted every time interval T(i) of the measuring time and the number of particles is referred to as Nj(i), where i=1, 2, ... 6 and j=1, 2, ... 16, as shown in FIG. 6 (step S4).

Figure 7:
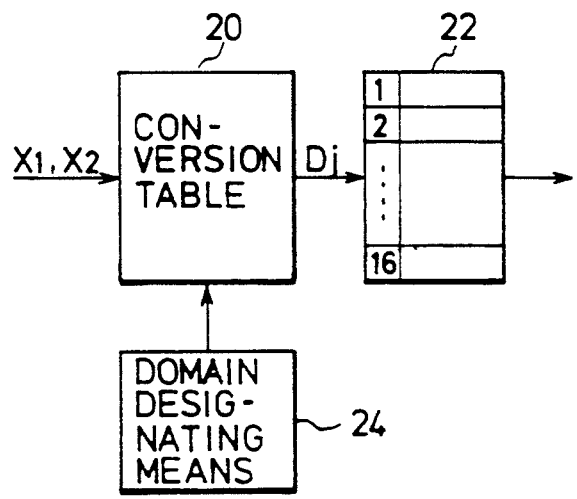
FIG. 7 is a block diagram showing a functional configuration of the microcomputer in the device of FIG. 2.

In order to count the particles, the microcomputer 16 includes a conversion table 20 as shown in FIG. 7. The conversion table 20 receives the measured data X of the respective particles and supplies signals Dj indicative of the domains Dj including their co-ordinates ($X_1$, $X_2$) in the above-mentioned co-ordinate system to a memory 22. The memory 22 has sixteen addresses corresponding to the domains Dj of FIG. 5 and receives the signal Dj from the conversion table 20 as its address signal to increment the stored value in the corresponding address by one every time. Thus, the number Nj(i) of the particles included in each domain Dj within each time interval T(i) is obtained.

The above-mentioned area to be partitioned need not always include all of the distributed particles and may be limited only to an especially noticeable area. Moreover, the number of domains (sixteen, here) and the partitioning pattern (checker board, here) may be selected arbitrarily. For this purpose, the microcomputer 16 further includes domain setting means 24 as shown in FIG. 7. When a produced distribution diagram is displayed with the display device 18 and an arbitrary area is then designated on the distribution diagram with a pointing device (not shown), a corresponding designating information is supplied through the domain setting means 24 to the conversion table 20 and the conversion table 20 responds to the measured data in this area to provide a corresponding address signal.

Figure 8:
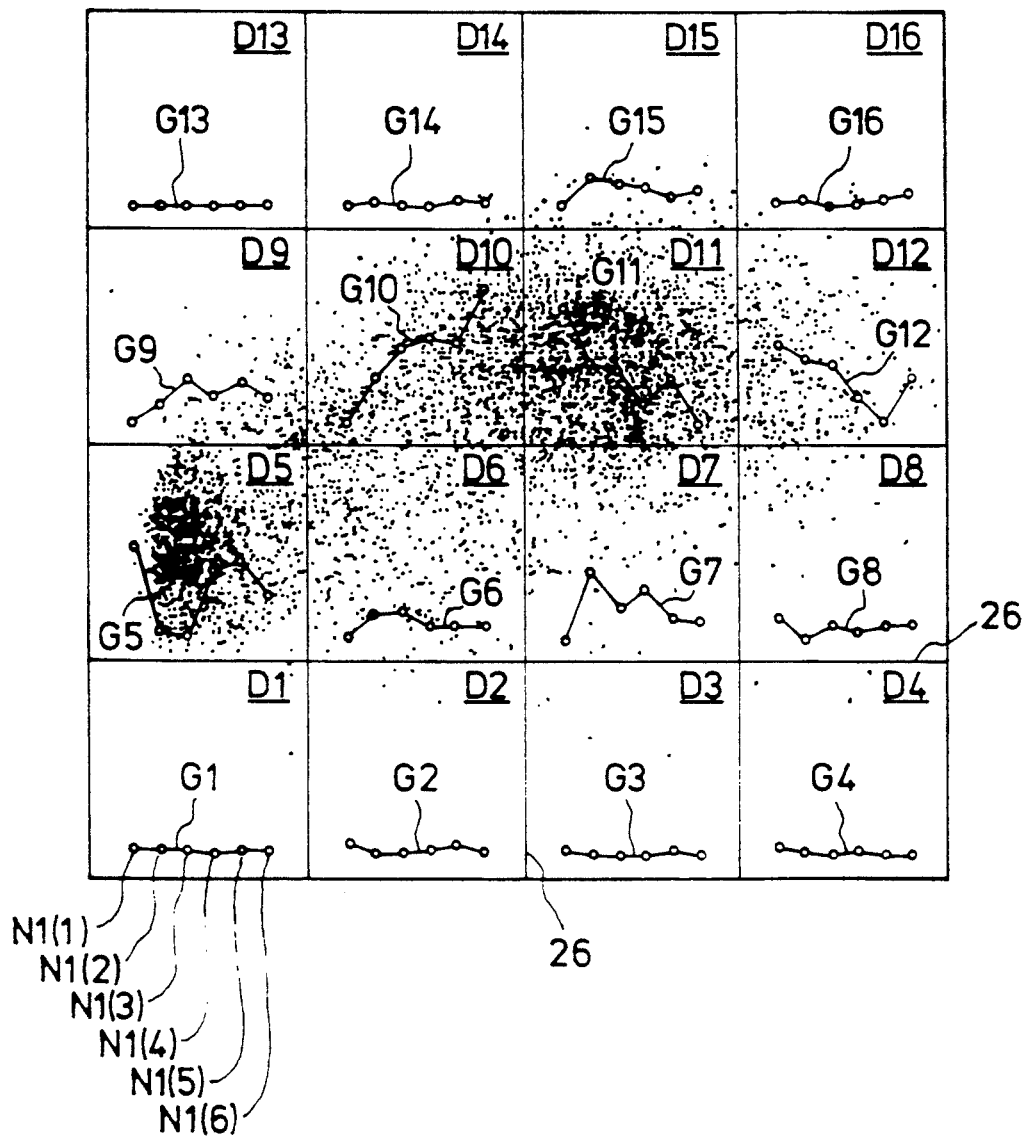
FIG. 8 is a diagram showing an example of the display pattern obtained in accordance with the method of this invention.

Next, the time-related change of the number Nj(i) of the particles within each domain, namely, the change with increase in the value of i is displayed, as shown in FIG. 8, in the form of broken line graph Gj, where j=1, 2, ... 16. At this time, the number of particles Nj(i) is scaled previously in order to have each broken line graph Gj included appropriately within the boundaries of the corresponding domain Dj (step S5). To this end, a difference between the maximum and minimum values of the available number of particle Nj(i) is calculated and the abscissa is graduated so that the difference corresponds to a sumtable size which is less than the vertical size of the domain. In addition, six time graduations corresponding to the time intervals T(i) are suitably determined on the ordinate axis.

Finally, the distribution diagram of FIG. 1 produced in step S2 is displayed on a display screen of the display device 18 (step S6) and the boundaries 26 of the domains of FIG. 5 are also displayed (step S7). The number of particles Nj(i) in each time interval T(i) is plotted in each domain Dj in accordance with the graduations of both axes determined in step S5 to form a broken line graph Gj which is then displayed in superposition with the distribution diagram having the boundaries 26 (step S8).

As is obvious from FIG. 8, the distribution diagram displayed as above serves to identify the clusters of various particles from the state of distribution of dots thereof and facilitate understanding of the time-related change of the number of particles from the broken line graph belonging to the corresponding cluster. In FIG. 8, for example, the number of particles in the domain D10 increases with time, while those in the domains D11 and D12 decrease with time. It is understood therefrom that the cluster of granulocytes distributed near the center of the drawing is moving leftwards in the drawing with a lapse of time. This method is also preferable for studying a time-related change of cells which may appear when some agent is applied to the cells.

The above embodiment has been given for illustrative purpose only and is not intended as any limitation of the invention. It should be obvious to those skilled in the art that various modifications and variations can be made thereon within the spirit and scope of the invention as defined in the appended claims. For example, while forward and sideward scattered light intensities were used in the above embodiment as the items of measurement of the measured data X, namely, the characteristic parameter $X_1$ and $X_2$, fluorescent intensity obtained by dyeing the particles with fluorescent dye may be used in combination therewith. High frequency impedance and d.c. impedance may be used also. Moreover, it is possible to use three or more characteristic parameters and display a change in three or higher dimension.

I claim:

1. A method of displaying a multi-dimensional distribution of particles comprising the steps of:

measuring at least two characteristic parameters of each particle for a predetermined measuring time to provide a sequence of measured data consisting of measured values thereof, dividing said measuring time into a plurality of time intervals, plotting said measured data in a coordinate space having said characteristic parameters as coordinate axes thereof to form a spatial distribution of the particles, partitioning said coordinate space into a plurality of domains, calculating a number of particles which are measured within each said time interval and included in each said domain, displaying said spatial distribution of the particles and boundaries of said domains, and displaying changes in the number of particles included in each said domain along respective time intervals.

2. A method as in claim 1, and further comprising the step of:

arranging said domains in a checker board pattern.

3. A method as in claim 1, and further comprising the step of:

displaying said charges of the number of particles in each said domain as a broken line graph.

* * * * *